US007442936B2

(12) United States Patent
Reischman et al.

(10) Patent No.: US 7,442,936 B2
(45) Date of Patent: Oct. 28, 2008

(54) INFRARED SPECTROSCOPY METHOD FOR MEASURING THE BASE NUMBER OF OVERBASED LUBRICANTS

(75) Inventors: P. Thomas Reischman, Lambertville, NJ (US); John S. Szobota, Morristown, NJ (US)

(73) Assignee: Exxonmobil Research and Engineering Company, Annandale, NJ (US)

(*) Notice: Subject to any disclaimer, the term of this patent is extended or adjusted under 35 U.S.C. 154(b) by 20 days.

(21) Appl. No.: 11/713,407

(22) Filed: Mar. 2, 2007

(65) Prior Publication Data
US 2007/0228281 A1 Oct. 4, 2007

Related U.S. Application Data

(60) Provisional application No. 60/788,236, filed on Mar. 31, 2006.

(51) Int. Cl.
*G01J 5/02* (2006.01)
(52) U.S. Cl. .................. 250/343; 250/339.12
(58) Field of Classification Search ............ 250/343, 250/339.12, 339.11; 436/61, 60; 73/53.05
See application file for complete search history.

(56) References Cited

U.S. PATENT DOCUMENTS 4,780,224 A * 10/1988 Jao .................. 508/401
5,537,336 A * 7/1996 Joyce .................. 702/108
6,642,191 B2 11/2003 Palazzotto et al.
6,756,348 B2 6/2004 Palazzotto et al.
2001/0013247 A1* 8/2001 Wilson et al. ............ 73/54.01
2003/0164451 A1 9/2003 Reischman et al.
2004/0142827 A1 7/2004 Palazzotto et al.
2005/0124074 A1 6/2005 Shelley et al.
2007/0084271 A1* 4/2007 Boyle et al. .............. 73/53.05

FOREIGN PATENT DOCUMENTS

| DE | 243 349 A1 | 2/1987 |
| FR | 2486246 | 1/1982 |
| JP | 05296926 | 11/1993 |
| JP | 10298583 | 4/1997 |
| JP | 2002350339 | 12/2002 |
| WO | WO03/073075 A2 | 9/2003 |

OTHER PUBLICATIONS

Neil Robinson, "Monitoring Oil Degradation with Infrared Spectroscopy", *Wear Check*—Technical Bulletin, Issue 18, 1998.
K. Kudlaty, et al., "In situ Analysis of Lubricating Oil Aging Using ATR-IR Sensors", VDI-Berichte, 1829, 2004, pp. 767-770 (Abstract—only German available).

(Continued)

*Primary Examiner*—David P. Porta
*Assistant Examiner*—Faye Boosalis
(74) *Attorney, Agent, or Firm*—Gary P. Katz

(57) ABSTRACT

The present invention provides a method for measuring a lubricant's total basicity by measuring one or more preselected infrared absorption bands of a lubricant and correlating the measured bands to the basicity. Preferably, the measured bands are due to carbonate or sulfate species in the lubricant.

3 Claims, 3 Drawing Sheets

OTHER PUBLICATIONS

Erwin Yacoub-George, et al., "High Speed Analysis of Used Hydrocarbons, Particularly Waste Oils", *Texte—Umweltbundesamt*, 2002, 76, i-iii, 1-80 (Abstract—only German available).

Roxana Badulescu, et al., "Quantitative Analysis of Additives in Lubricants", *Revista de Chimie* (Bucharest, Romania), 2003, 54(6), pp. 519-521.

Federica M. Piras, et al., "Combined in situ (ATR FT-IR) and ex situ (XPS) Study of the AnDTP-iron Surface Interaction", *Tribology Letters*, 2003, 15(3), pp. 181-191.

Federica M. Piras, et al., "In situ Attenuated Total Reflection (ATR) Spectroscopic Analysis of Tribological Phenomena", Tribology Series, 28th Leeds-Lyon Symposium on Triboloby, Vienna, Sep. 4-7, 2001, 2002, pp. 199-206.

Thomas E. Tiwald, "Determination of the Mid-IR Optical Constants of Water and Lubricants Using IR Ellipsometry Combined with an ATR Cell", *Thin Solid Films*, 313-314, 1998, pp. 718-721.

Sarjant Singh, "Troubleshooting Aircraft Problems Using FT-IR", *Spectroscopy*, 1995, 10(3), pp. 36-38.

Jun Dong, "Quantitative Condition Monitoring of Lubricating Oils by Fourier Transform Infrared (FTIR) Spectroscopy", McGill University Dissertation, 2001, 165 pages.

F. R. Van de Voort, et al., "Determination of Acid Number and Base Number in Lubricants by Fourier Transform Infrared Spectroscopy", *Applied Spectroscopy*, 57(11), 2003, pp. 1425-1431.

M. Kato, et al., "Evaluation of Useful Lifetime of Gas Engine Lubrication Oils—Suggestion of New Methods of Oil Analysis and Evaluation of Degradation of Full-Synthetic Long Life Lubrication Oils", Journal of the Japan Petroleum Institute, 45/1, Jan. 2002, pp. 1-9 (Abstract—Japanese only).

Jun Dong, et al., "Determination of Total Base Number (TBN) in Lubricating Oils by Mid-FTIR Spectroscopy", *Journal of the Society of Tribologists and Lubrication Engineers*, Nov. 2001, pp. 24-30.

J. Baladincz, et al., "Interactions of Additives in Lubricating Oil Compositions", *Hungarian Journal of Industrial Chemistry*, V26, N. 2, pp. 155-159 (1998), (Abstract Only).

Carlton S. Joyce, "Tandem Spectometers an On-Site Analyzer", *ICE*, 1997, 28-3, vol. 3, pp. 23-28.

Ernest R. Marshall, "Used Oil Analysis—A Vital part of Maintenance", *Lubrication*, V79, N. 2, 1993, pp. 1-12.

Katarzyna Kudlaty, "Development of an Infrared Sensor for On-Line Analysis of Lubricant Deterioration", 2nd IEEE International Conference on Sensors, New York, Oct. 22, 2003, vol. 12, pp. 903-908.

* cited by examiner

Figure 3

TBN versus Net Integrated Area Sulfate Band (1279 to 1022 cm$^{-1}$)

Regression Line R squared = 0.964

Net Integrated Area Sulfate Band (1279 to 1022 cm$^{-1}$)

INFRARED SPECTROSCOPY METHOD FOR MEASURING THE BASE NUMBER OF OVERBASED LUBRICANTS

This application claims priority of Provisional Application 60/788,236 filed Mar. 31, 2006.

FIELD OF THE INVENTION

The present invention relates to a method for measuring a lubricant's basicity. More specifically, the present invention relates to a spectroscopic method for measuring the total base number (TBN) of overbased lubricants.

BACKGROUND OF THE INVENTION

As is known, the total base number (TBN) of a lubricating oil is an important indicator of oil condition. For example, during combustion of fuel in an engine, sulfur in the fuel is ultimately converted to sulfuric acid which if not neutralized will significantly increase the wear and corrosion of the engine components.

Lubricating oils are formulated to be highly alkaline in order to neutralize the acids formed during the combustion process. Indeed, lubricating oils are routinely "overbased" with calcium carbonate.

The recommended range of an oil's TBN depends in part on the range of sulfur levels in the fuel being burned. Thus overbased lubricants are particularly important for marine and stationary power plant engine applications because high sulfur fuel is often burned in these engines.

The ability to monitor the TBN of an oil is quite useful in evaluating whether the oil can continue to meet its intended function.

TBN is reported in terms of milligrams of potassium hydroxide (equivalent) per gram of lubricant (mgKOH/g), reflecting the acid neutralizing capacity relative to the strong base. Standard laboratory methods for determing TBN are ASTM D2896 and D4739. The conventional method used in the marine industry for both new and used oils is D2896.

In WO 03/073075 A2 there is disclosed a method for determining the TBN of an oil by measuring one or more selected infrared absorption bands of the oil and correlating the measured bands with the TBN. While this technique is useful in determining an oil's TBN without knowing the TBN of a fresh oil, its accuracy has a lower limit of 20 mgKOH/g.

It would be advantageous to provide a TBN measuring method that is amenable to onsite, online and inline measurement of lubricating oil and that is accurate over the entire range of TBN levels for overbased lubricants, nominally 0 to 100 mgKOH/g.

SUMMARY OF THE INVENTION

Broadly stated, the present invention comprises measuring one or more pre-selected infrared absorption bands of an oil using attenuated total reflectance infrared spectroscopy (ATR IR) and correlating the absorbance measured bands to the TBN, either at a single frequency or integrated over multiple frequencies. Specifically, the bands measured are those due to the carbonate or sulfate species in the oil.

DETAILED DESCRIPTION OF THE INVENTION

By way of overview, attenuated total reflectance infrared spectroscopy is utilized in the present invention to monitor the presence of carbonate or sulfate species in a lubricant which then is correlated to the TBN of the lubricant.

The present invention may be applied to fresh or in-use lubricants although their respective calibration lines may be different. The method is suitable for use in a laboratory and importantly in the field and is readily adaptable for use online.

It has been discovered that carbonate infrared absorption bands in the frequency range at 1524-1400 $cm^{-1}$, at about 863 $cm^{-1}$ and at about 683 $cm^{-1}$ correlate with TBN. Thus in one embodiment of the present invention, the TBN of a lubricant is determined by measuring the infrared spectrum of the lubricant using ATR IR. At least one of the absorption bands for the carbonate species is then selected. The measured absorbance (single or multiple frequencies) at the selected band is then correlated to the oil's TBN. Correlation lines are developed by comparing the absorbance for this selected band for samples on which TBN has been measured by a standard method and finding the best linear fit through the data. Again, calibrations for fresh and in-use lubricants may be different.

In another embodiment of the invention, the sulfate absorption band at a frequency of 1279-1022 $cm^{-1}$ also shows good correlation with TBN for in-use lubricants and hence can be used in the same way as the carbonate bands described above for measuring an oil's TBN.

Lubricating oils used in marine and stationary power plant engines are overbased with carbonate. Therefore, it is particularly preferred in the practice of the invention to determine the TBN of those oils by measuring a carbonate band, and it is most preferred to measure the band in the range of 1524-1400 $cm^{-1}$.

The carbonate absorption band in the 1524-1400 $cm^{-1}$ region has within it (1475-1400 $cm^{-1}$) a strong band due to hydrocarbons which remain substantially constant at all TBN levels. Consequently, the carbonate band can be easily integrated by summing the absorbances over the frequency range.

Optionally, infrared filters may be used, for example, to exclude the hydrocarbon band at 1475-1440 $cm^{-1}$ or to monitor only a portion of the broad carbonate band in the 1524-1400 $cm^{-1}$ region. In instances where filters are used for isolating the carbonate band, separate correlation lines are required for new and used lubricants.

EXAMPLES

A series of scrapedown (used) cylinder oils and a fresh cylinder oil were analyzed by ATR IR. The TBN levels of the oils as measured by ASTM D2896 ranged from 5 to 71 mgKOH/g.

Figure 1:
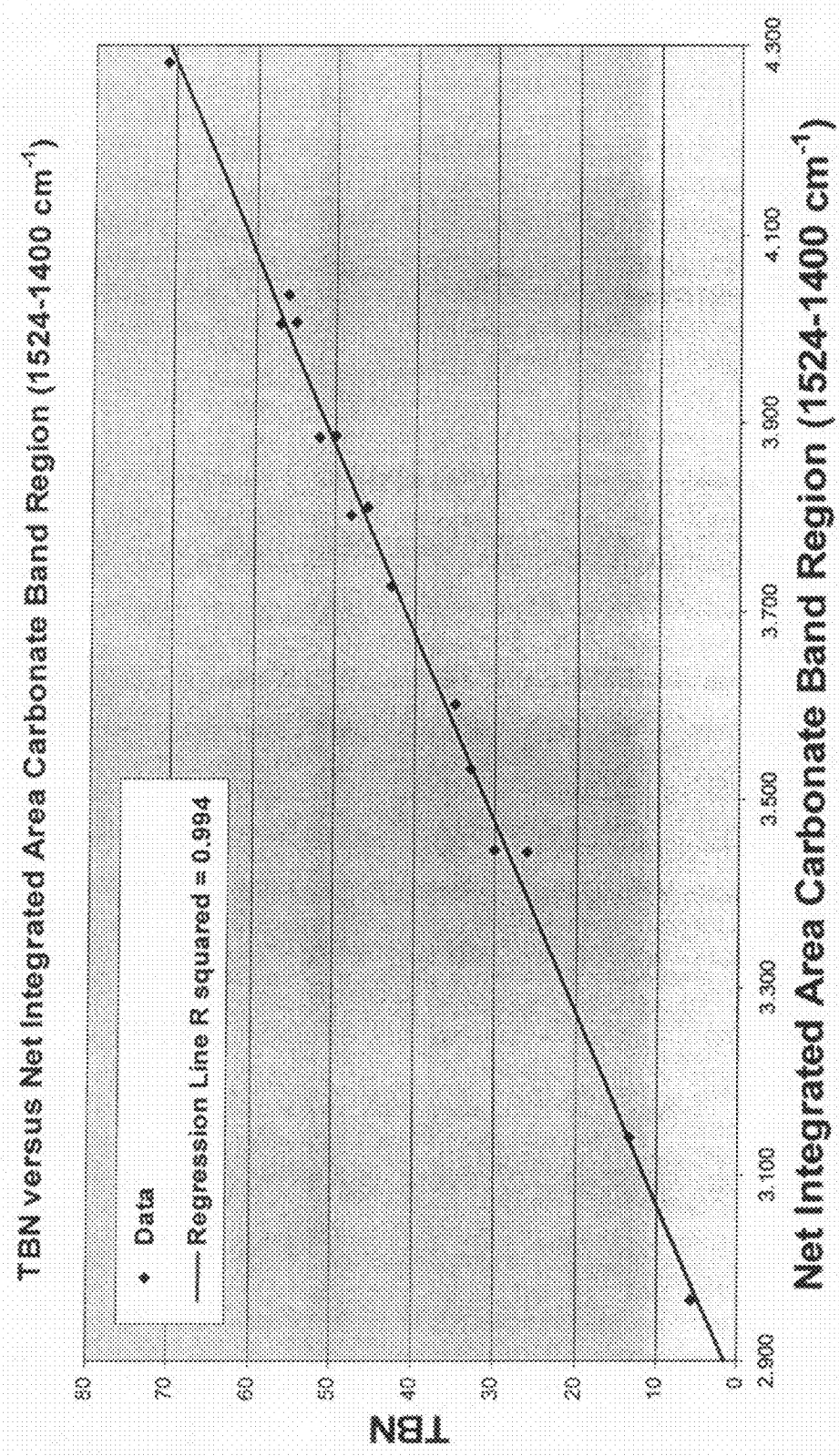
FIGS. 1 and 2, which show the correlation of carbonate IR absorbance with TBN, and FIG. 3, which shows the correlation of sulfate IR absorbance with TBN, illustrate the invention.
Figure 2:
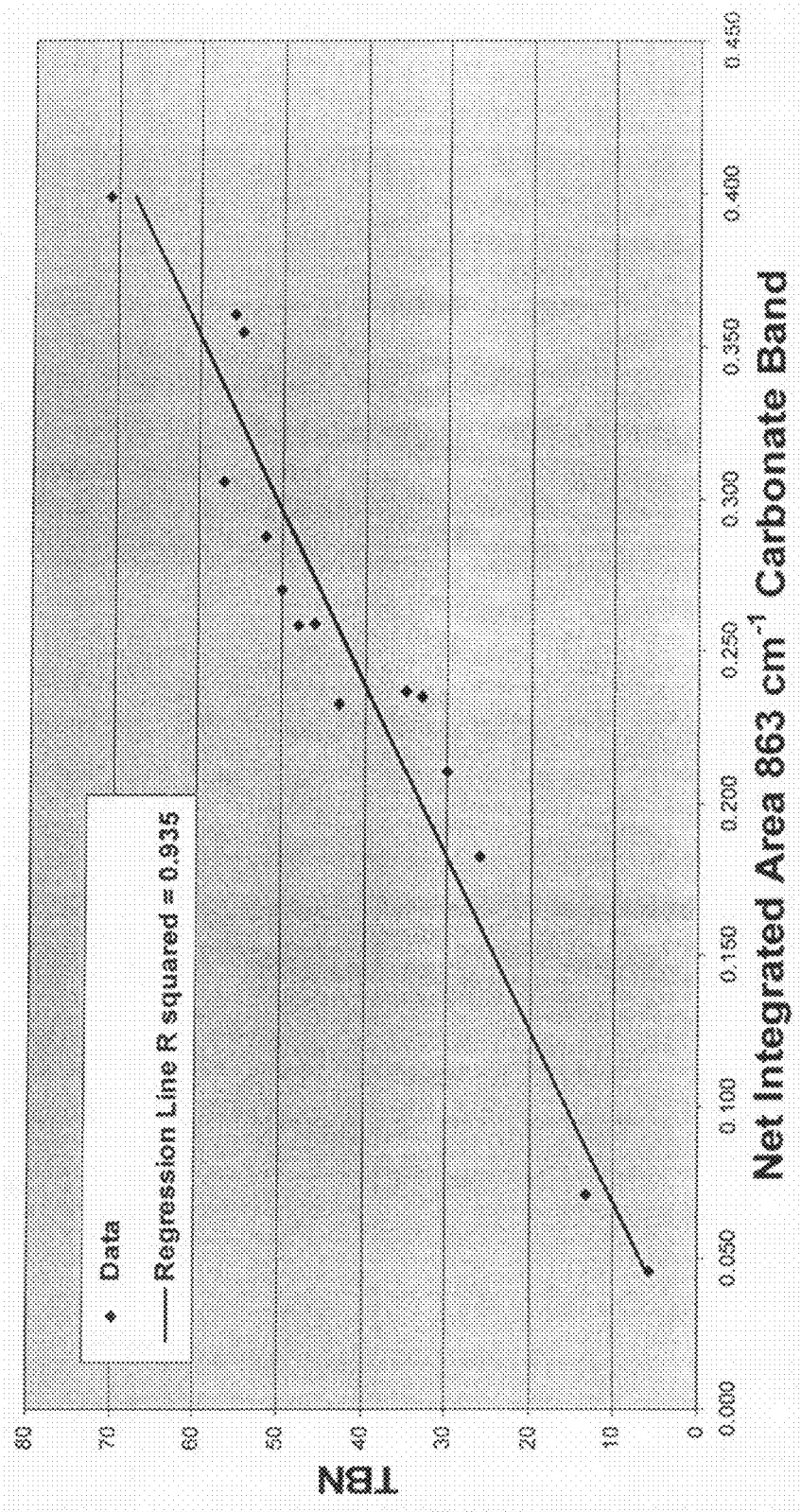

Carbonate bands were integrated at 1524-1400 $cm^{-1}$ and at about 863 $cm^{-1}$ and a sulfate band at 1279-1022 $cm^{-1}$ was also integrated. FIGS. 1 and 2 show the correlation of carbonate IR absorbance with TBN. FIG. 3 shows the sulfate IR absorbance with TBN.

What is claimed is:

1. A method that is suitable for determining the TBN of an overbased lubricant composition over the entire range of TBN levels for overbased lubricants, the method comprising:

measuring one or more pre-selected infrared absorption bands of the lubricant using ATR IR wherein the absorption bands are in the range of 1524-1400 cm$^{-1}$, about 863 cm$^{-1}$ and about 683 cm$^{-1}$; and correlating the absorbance of the measured bands to the lubricant TBN.

2. The method of claim 1 wherein the bands are between 1524-1400 cm$^{-1}$.

3. The method of claim 1 wherein the band is at about 863 cm$^{-1}$.

* * * * *